US008000795B2

(12) United States Patent  (10) Patent No.: US 8,000,795 B2
Lozano  (45) Date of Patent: Aug. 16, 2011

(54) COGNITIVE FUNCTION WITHIN A HUMAN BRAIN

(76) Inventor: Andres M. Lozano, Toronto (CA)

(*) Notice: Subject to any disclaimer, the term of this patent is extended or adjusted under 35 U.S.C. 154(b) by 0 days.

(21) Appl. No.: 11/303,293

(22) Filed: Dec. 16, 2005

(65) Prior Publication Data

US 2007/0060974 A1    Mar. 15, 2007

Related U.S. Application Data

(60) Provisional application No. 60/636,988, filed on Dec. 17, 2004.

(51) Int. Cl.
*A61N 1/36* (2006.01)
(52) U.S. Cl. .......................................... 607/45
(58) Field of Classification Search ............... 607/2, 45, 607/115, 116; 600/373, 377, 378, 383
See application file for complete search history.

(56) References Cited

U.S. PATENT DOCUMENTS

| | | | | |
|---|---|---|---|---|
| 5,683,422 A | * | 11/1997 | Rise | 607/2 |
| 5,938,688 A | * | 8/1999 | Schiff | 607/45 |
| 6,128,537 A | * | 10/2000 | Rise | 607/45 |
| 6,556,868 B2 | * | 4/2003 | Naritoku et al. | 607/45 |
| 2002/0151939 A1 | * | 10/2002 | Rezai | 607/40 |
| 2003/0097159 A1 | * | 5/2003 | Schiff et al. | 607/45 |
| 2004/0172091 A1 | * | 9/2004 | Rezai | 607/45 |
| 2005/0119712 A1 | * | 6/2005 | Shafer | 607/45 |
| 2006/0100671 A1 | * | 5/2006 | Ridder | 607/45 |

OTHER PUBLICATIONS

"MS Glossary", From Internet Jan. 19, 2010. Teva Pharmaceutical Industries, Ltd. <http://www.copaxone.com/aboutMS/glossary.aspx#>.*
"Institute for Neurodegenerative Disorders", Homepage. From Internet Jan. 19, 2010. <http://www.indd.org/>.*
"Mass General Institute for Neurodegenerative Disease", Homepage. From Internet Jan. 19, 2010. <http://www.mghmind.org/>.*
Sircar, Sabyasachi. "Principles of Medical Physiology", 2008, Georg Thieme Verlag, p. 681.*
Cytowic, Richard E. "The Neurological Side of Neuropsychology,", 1996, Massachusetts Institute of Technology. pp. 99-101.*
Wikipedia, "Neurodegenerative Disease", From Internet Jan. 19, 2010. Wikipedia Foundation, Inc.*

* cited by examiner

*Primary Examiner* — Carl H Layno
*Assistant Examiner* — Gary A Porter, Jr.
(74) *Attorney, Agent, or Firm* — Kilpatrick Townsend & Stockton LLP

(57) ABSTRACT

Methods and apparatus for improving cognitive function within a human. The invention utilizes an implanted device, such as an implantable signal generator or an implantable pump, to affect tissue elements within a Papez circuit of the human brain as well as tissue upstream or downstream from the Papez circuit. The implanted device delivers treatment therapy to thereby improve cognitive function by the human. A sensor may be used to detect various symptoms of the cognitive disorder. A microprocessor algorithm may then analyze the output from the sensor to regulate delivery of the stimulation and/or drug therapy.

27 Claims, 6 Drawing Sheets

COGNITIVE FUNCTION WITHIN A HUMAN BRAIN

This patent application claims priority to U.S. Provisional Application Ser. No. 60/636,988 filed Dec. 17, 2004, which is incorporated herein by reference in its entirety.

FIELD OF THE INVENTION

The present invention relates to techniques for providing treatment therapy to improve cognitive function within a brain of a human by way of brain stimulation and/or drug infusion.

BACKGROUND OF THE INVENTION

Cognitive disorders are a common type of neurological disorders. For example, dementia is form of impaired cognition caused by brain dysfunction. The hallmark of most forms of dementia is the disruption of memory performance. Among the several conditions labeled as dementia, the most common are Alzheimer's disease and mild cognitive impairment (MCI), which is a pre-clinical form of Alzheimer's disease. MCI is an intermediate state between normal aging and dementia and is characterized by acquired cognitive deficits, without significant decline in functional activities of daily living. Subjects with MCI and the initial phase of Alzheimer's disease originally present with a predominant deficit in memory function. In more advanced stages of Alzheimer's disease, impairment in additional cognitive domains culminate with a significant decline in quality of life and the inability to perform usual daily activities.

Alzheimer's disease is one of the most common cognitive disorders in humans and has an exponentially increasing incidence. Although the defining characteristic of Alzheimer's disease is cognitive impairment, it is often accompanied by mood and behavioral symptoms such as depression, anxiety, irritability, inappropriate behavior, sleep disturbance, psychosis, and agitation. Neuro-imaging and genetic testing have aided in the identification of individuals at increased risk for dementia. However, the measurement of change in cognitive and functional status in, for example, MCI remains challenging because it requires instruments that are more sensitive and specific than those considered adequate for research in dementia. Accordingly, no treatment exists that adequately prevents or cures Alzheimer's disease or MCI.

Alzheimer's disease and MCI are already a public health problem of enormous proportions. It is estimated that 5 million people currently suffer with Alzheimer's disease in the United States. This figure is likely underestimated due to the high number of unrecognized and undiagnosed patients in the community. By the year 2050, Alzheimer's is projected to affect 14 million people. Moreover, because the prevalence of Alzheimer's disease doubles every 5 years after age 65, the impact of the disease on society tends to increase with the growth of the elderly population. The annual cost in the United States of AD alone is approximately $100 billion.

There is currently no effective treatment for the memory loss and other cognitive deficits presented by patients with dementia, particularly Alzheimer's disease. Treating Alzheimer's disease tends to be more challenging than other neurological disorders because Alzheimer's largely affects a geriatric population. Oral medications including Acetylcholinesterase inhibitors and cholinergic agents are the mainstay treatment for this condition. Nevertheless, the outcome with these agents is modest and tends to decline as the disease progresses. Other agents, such as nonsteroidal anti-inflammatory drugs, corticosteroids, COX-2 inhibitors, estrogen, and antioxidants, have also been tried with poor results. Neurotrophic factors (molecules that increase survival and growth of neurons in laboratory experiments) have been recently used clinically for Alzheimer's disease. Because these agents are proteins, they are inactive with oral administration and cannot cross the blood-brain barrier when administered systemically. When infused intraventricularly in three patients with Alzheimer's disease, nerve growth factor (NGF) increased cerebral nicotine binding. However, this compound had only modest clinical effects and was associated with back pain and weight loss that were reversible with the cessation of treatment.

Alternative routes of neurotrophic factor administration are currently being studied. Gene therapy and small neurotrophic molecules that can penetrate the blood-brain barrier (AIT-082) are possible methods for drug delivery. Moreover, treatment strategies against beta-amyloid protein accumulation and plaque formation including immunotherapies with vaccines are other possible methods. However, but clinical data is still lacking for any of these alternative methods for treating cognitive disorders.

Most aspects of memory function involve temporal lobe structures. Amnesic syndromes have been described after the disruption of the hippocampus, amygdala, fornix, mammillary bodies, anterior nucleus of the thalamus, rhinal cortex, parahippocampal cortex, and temporal neocortex. These structures are mainly involved with the so-called declarative memory, which comprises the memory for facts, events, spatial location, recognition of forms, significance of data processed, among others. However, no interventions within the temporal lobe have been successful in improving memory function.

The hippocampus also has been found to play a crucial role in learning and memory. Lesions of the hippocampus in rodents, primates and man have been found to impair the process of memory acquisition and its persistence. In addition, the hippocampus receive strong inputs from nuclei in the basal forebrain, including the septal nuclei, the diagonal band of Broca and the nucleus basalis of Meynert and lesions in these structures also impair learning and memory. Dysfunction or pathological changes in these circuits may contribute to memory and learning deficits in a variety of circumstances including old age and Alzheimer's disease. The finding of pathological changes in these structures (including synaptic and neuronal loss, senile plaques and neurofibrillary tangles) is characteristic of both age related and Alzheimer's type memory and learning dysfunction. Since septohippocampal lesions affect new learning to a greater extent than established memories, these structures appear to play an essential facilitory role in the establishment and consolidation of memory. Again, however, no interventions within the hippocampus or related structures have been successful in improving memory function.

It is therefore desirable to provide a technique for preventing or treating cognitive disorders such as Alzheimer's disease and/or, more broadly, to improve cognitive function in patients.

BRIEF SUMMARY OF THE INVENTION

An embodiment of the invention uses electrical stimulation of the Papez circuit and/or tissue upstream to or downstream from the Papez circuit to improve cognitive function. The treatment is carried out by an implantable signal generator and at least one implantable electrode having a proximal end coupled to the signal generator and having a stimulation portion for electrically affecting tissue elements of a Papez circuit or upstream/downstream tissue. Alternatively, the treatment may be carried out by an implantable pump and at least one catheter having a proximal end coupled to the pump and having a discharge portion for infusing therapeutic dosages of the one or more drugs into a predetermined infusion site in neural tissue. By using the foregoing techniques, cognitive function within a human can be significantly improved including, for example, patients suffering from Alzheimer's and MCI. In other embodiments of the invention, drug infusion may be used as treatment therapy in addition to the electrical stimulation.

In another embodiment of the invention, a sensor is used in combination with the signal generator and/or implantable pump to treat the cognitive disorder. In this form of the invention, the sensor generates a sensor signal related to extent of the cognitive disorder. The implanted device is responsive to the sensor signal to regulate the signal generator and/or pump so that the neurological disorder is treated.

By using the foregoing techniques, cognitive disorders can be controlled or treated to a degree unattainable by prior art methods or apparatus.

DETAILED DESCRIPTION OF THE INVENTION

The invention discloses techniques for delivering treatment therapy to Papez circuit of a human brain to improve cognitive function. The applicant has discovered that cognitive function can be improved through delivery of treatment therapy to the Papez circuit and/or tissue upstream to or downstream from the Papez circuit. Accordingly, the invention incorporates electrical stimulation and/or drug infusion techniques to directly or indirectly influence tissue elements within the Papez circuit. One or more electrodes and/or catheters are implanted in the brain so that the stimulation or infusion portions lie within or in communication with predetermined portions of the brain. The electrical stimulation or drug therapy influences the Papez circuit to achieve the desired result.

These techniques of the present invention are suitable for use within any implantable medical device. In an embodiment, the present invention is implemented within an implantable neurostimulator system, however, those skilled in the art will appreciate that the present invention may be implemented generally within any implantable medical device system including, but not limited to, implantable drug delivery systems, implantable systems providing stimulation and drug delivery.

In addition, the present invention may be embodied in various forms to analyze and treat cognitive disorders. Such disorders include, for example without limitation, Alzheimer's disease, MCI, dementia, amnesia and memory disorders as can occur after injury, trauma, stroke, cranial irradiation, and in the context of genetic, congenital, infectious, autoimmune, toxic (drugs and alcohol), nutritional (vitamin deficiencies) metabolic, inflammatory, neurodegenerative neoplastic or idiopathic processes involving the brain. Some additional specific disorders where the therapy of the invention may be useful include: amnestic syndromes, Werkicke-Korsakoff and Korsakoff syndromes, Herpes encephalitis, severe hypoxia, vascular disorders, head injury, transient global amnesia, global amnesia epileptic amnesia, cerebral palsy, autism, mental retardation and attention deficit and hyperactivity disorders.

Figure 1:
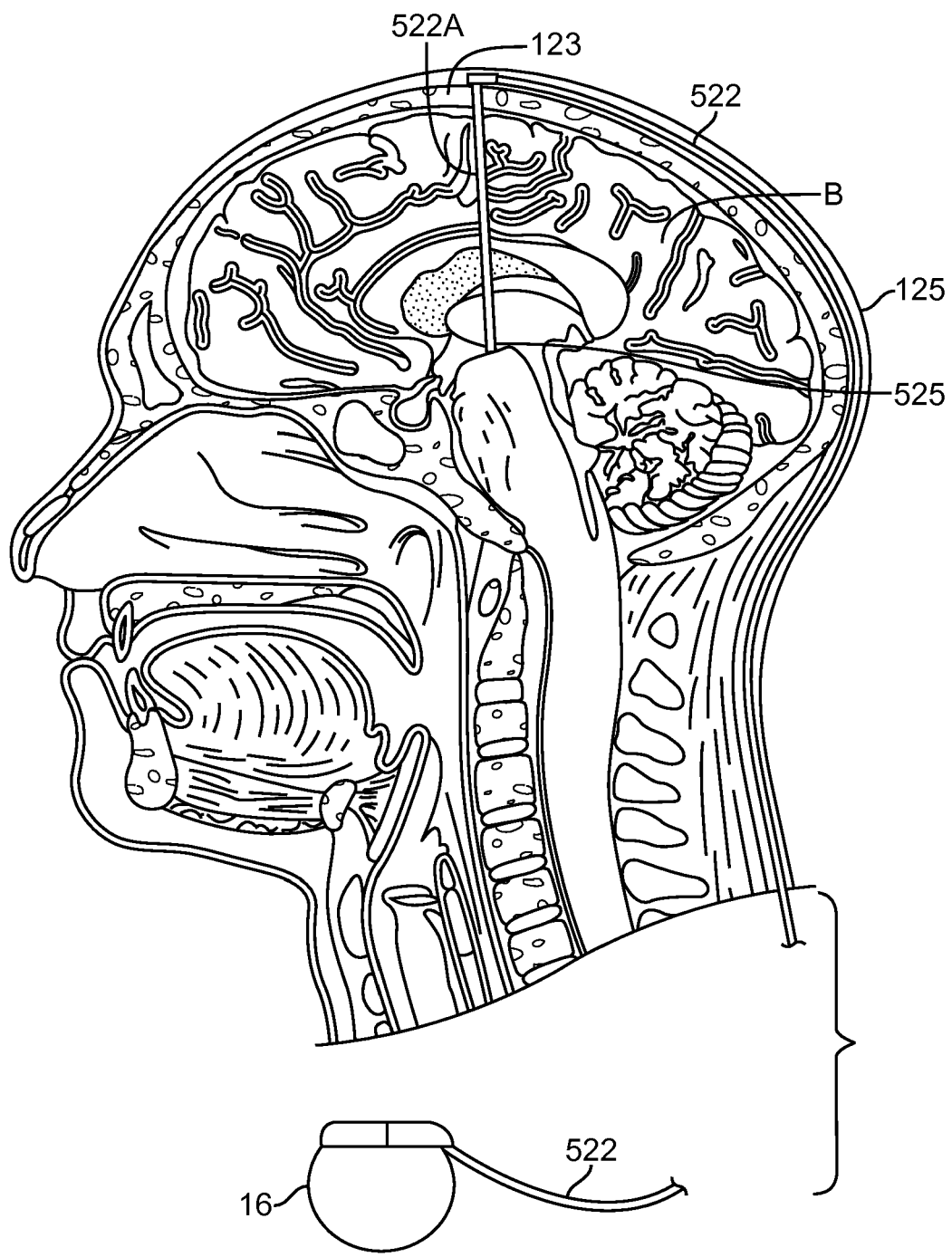
FIG. 1 is a diagrammatic illustration of an electrode implanted in a brain according to an embodiment of the present invention and a signal generator coupled to the electrode.

Referring to FIG. 1, an implantable neurostimulator device 16 made in accordance with an embodiment may be implanted below the skin of a patient. A lead 522A is positioned to stimulate a specific site 525 in a brain (B). Device 16 may take the form of a modified signal generator Model 7424 manufactured by Medtronic, Inc. under the trademark Itrel II which is incorporated by reference. Lead 522A may take the form of any of the leads sold with the Model 7424 such as Model 3387, for stimulating the brain, and is coupled to device 16 by a conventional conductor 522. One or more external programmers (not shown) may be utilized to program and/or communicate bi-directionally with the implanted device 16.

As shown, the distal end of lead 522A terminates in four stimulation electrodes implanted into a portion of the brain by conventional stereotactic surgical techniques. Each of the four electrodes is individually connected to device 16 through lead 522A and conductor 522. Lead 522A is surgically implanted through a hole in the skull 123 and conductor 522 is implanted between the skull and the scalp 125 as shown in FIG. 1. Conductor 522 is joined to implanted device 16 in the manner shown. Referring to FIG. 2A, device 16 is implanted in a human body 120 in the location shown. Body 120 includes arms 122 and 123. Alternatively, device 16 may be implanted in the abdomen. Conductor 522 may be divided into twin leads 522A and 522B that are implanted into the brain bilaterally as shown. Alternatively, lead 522B may be supplied with stimulating pulses from a separate conductor and signal generator. Leads 522A and 522B could be 1) two electrodes in two separate nuclei that potentiate each others effects or 2) nuclei with opposite effects with the stimulation being used to fine tune the response through opposing forces. It will be appreciated, however, that any number of electrodes may be implanted within the brain in accordance with the invention. Additionally, one or more secondary electrodes may be implanted so that a secondary stimulation portion lies in communication with another predetermined portion of a brain. Moreover, as will be discussed below, one or more catheters, coupled to a pump, may be implanted so that a secondary stimulation portion lies in communication with the tissue elements of the Papez circuit.

Figure 4:
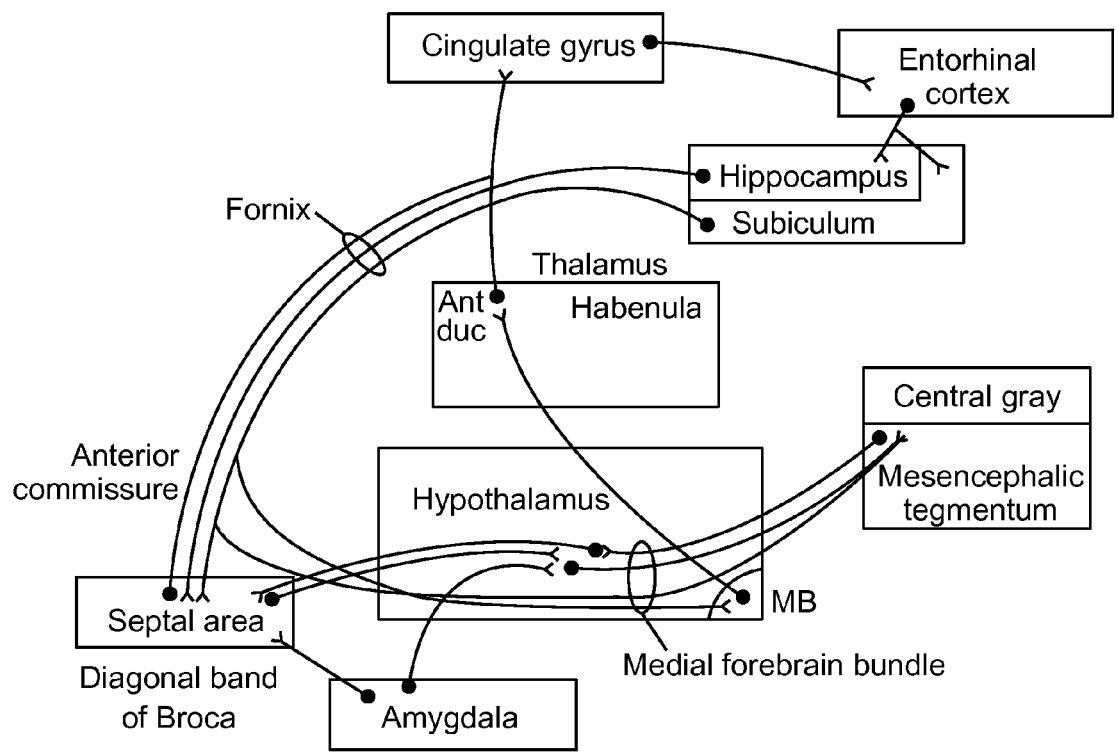
FIG. 4 is a diagram depicting the various components of the Papez circuit.
Figure 4A:
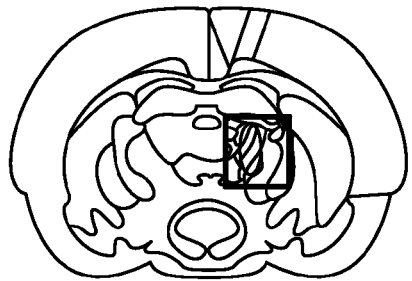
FIGS. 4(a) and 4(b) illustrate specific components of the Papez circuit.
Figure 4A:
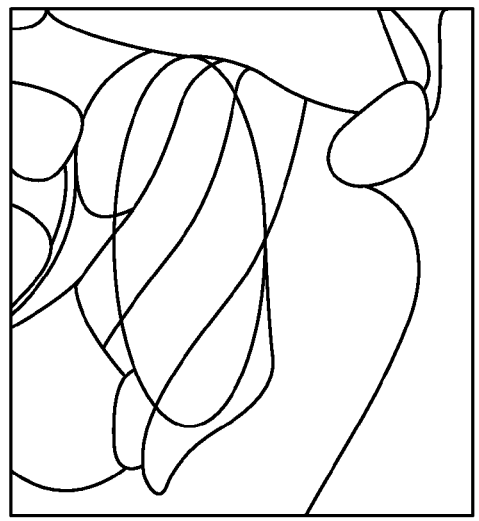
Figure 4B:
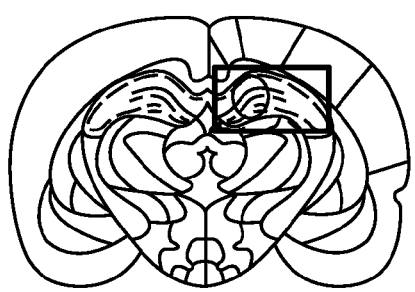
Figure 4B:
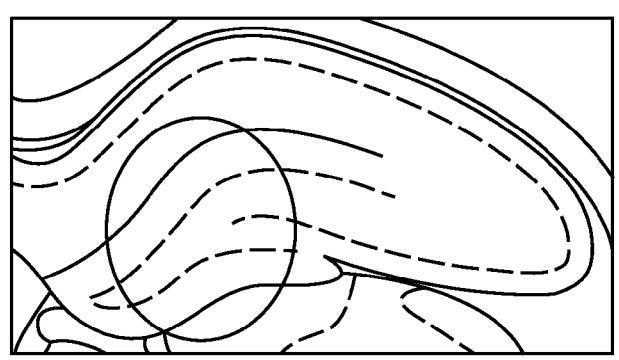

The targeted treatment site is the Papez circuit or, more generally, any site that affects neural tissue within the Papez circuit. The Papez circuit is generally a neuronal circuit in the limbic system, consisting of the hippocampus, fornix, mammillary body, anterior thalamic nuclei, and cingulated gyrus. FIG. 4 depicts the various elements of the Papez circuit. In an embodiment, hypothalamic stimulation with bilaterally implanted electrodes could modulate memory function and activate limbic structures. Hypothalamic stimulation may evoke sensations of déjà vu, vague flashes of memory, and result in a significant improvement in memory.

Moreover, the invention envisages the treatment of memory deficits through the electrical stimulation of brain locations that are upstream from the Papez circuit (i.e., structures that project to the Papez circuit) and/or downstream from the Papez circuit (i.e., structures that receive inputs from Papez circuit). For example, the treatment therapy may affect temporal lobe structures, namely the, the septal nuclei, the septo-hippocampal pathway, hippocampus; amygdala; fimbria/fornix; the hypothalamus including the mammilary bodies; the medial forebrain bundle, mammilothalamic tract; anterior and mediodorsal nuclei of the thalamus; entorhinal, perirhinal and parahippocampal cortices; temporal stem and temporal white matter; and temporal neocortex, the amygdala, the diagonal band of the Broca. In addition, stimulation could be applied to the cingulate cortex and to frontal lobe structures and to the basal forebrain. Because stimulation in the nervous system is though to affect mostly axonal projections and fiber pathways, an embodiment envisages stimulating the fornix or mammilothalamic tracts.

Examples of upstream structures that project onto the Papez circuit that could also be affected include the regions that provide input to the hippocampus such as nuclei in the basal forebrain, including the septal nuclei, the diagonal band of Broca and the nucleus basalis of Meynert. Each of these structures and the neural structures that in turn modify their activity (particularly, the locus ceruleus catecholaminergic system, the brainstem raphe serotonergic system, the brainstem cholinergic system and the mesolimbic dopaminergic system) are potential sites of intervention through the use of electrical stimulation or drug infusion to reward, reinforce and enhance learning and memory. As discussed herein, reference to the Papez circuit may also include tissue upstream to or downstream from the Papez circuit The device 16 may be operated to deliver stimulation to the tissue elements of the Papez circuit to thereby improve cognitive function by the human. The particular stimulation delivered may be performed by selecting amplitude, width and frequency of stimulation by the electrode. The possible stimulations include between 0 Hertz and 300 Hertz for frequency, between 0 Volts and 10 Volts for pulse amplitude, and between 0 μSeconds and 400 μSeconds for pulse width.

In an embodiment, bipolar stimulation of the hypothalamus may be utilized with the following stimulation parameters −2.8 V bilaterally, 60 μsec, and 130 Hz with contacts 0 and 4 as cathodes, and contacts 1 and 5 as anodes. In another embodiment, monopolar stimulation of the hypothalamus may be utilized with the following stimulation parameters −2.8 V bilaterally, 60 μsec, 130 Hz, contacts 0 and 4 as negative and the case as positive.

Figure 2:
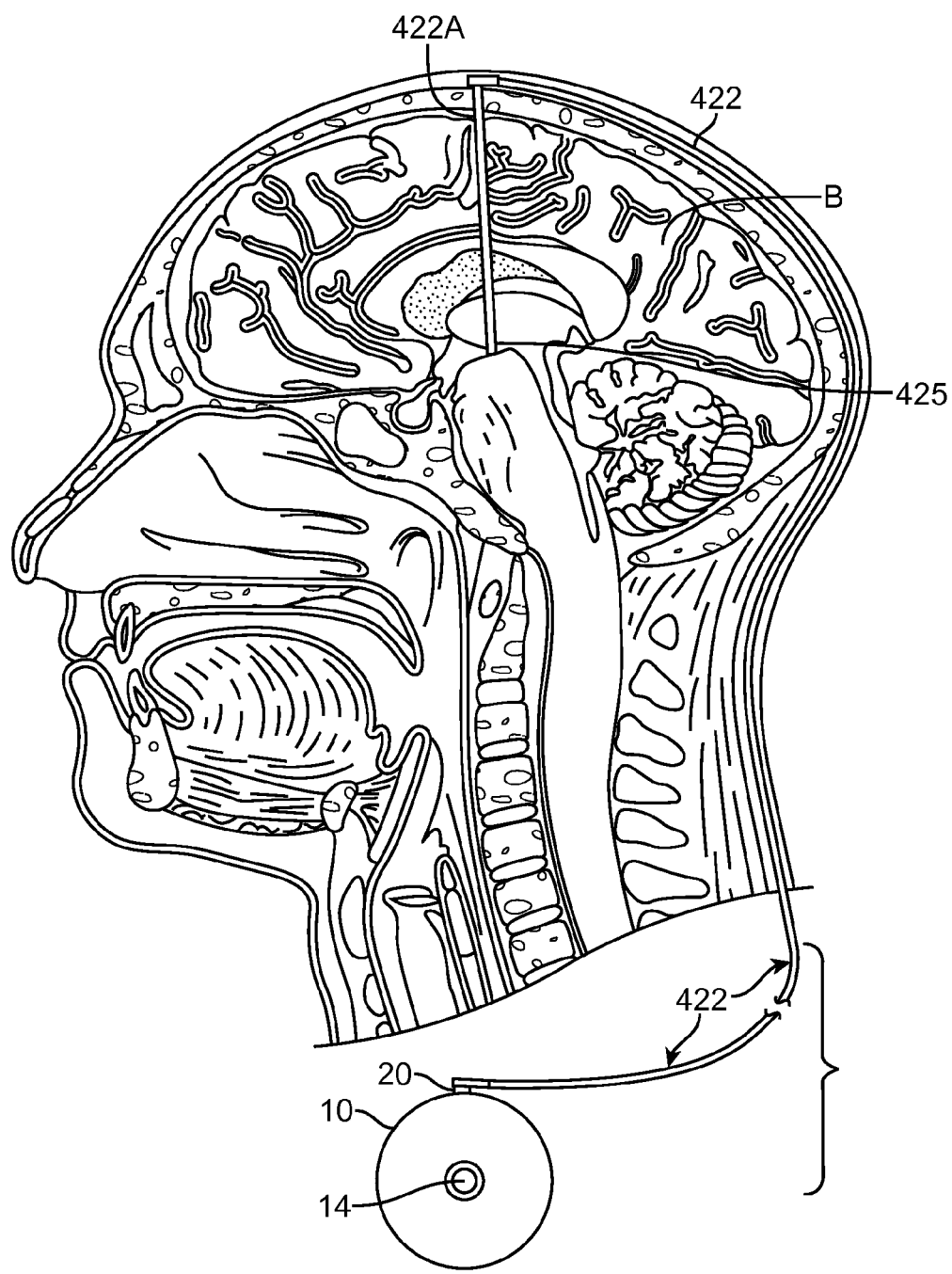
FIGS. 2 and 2A are diagrammatic illustrations of a catheter implanted in a brain according to an embodiment of the present invention.
Figure 2A:
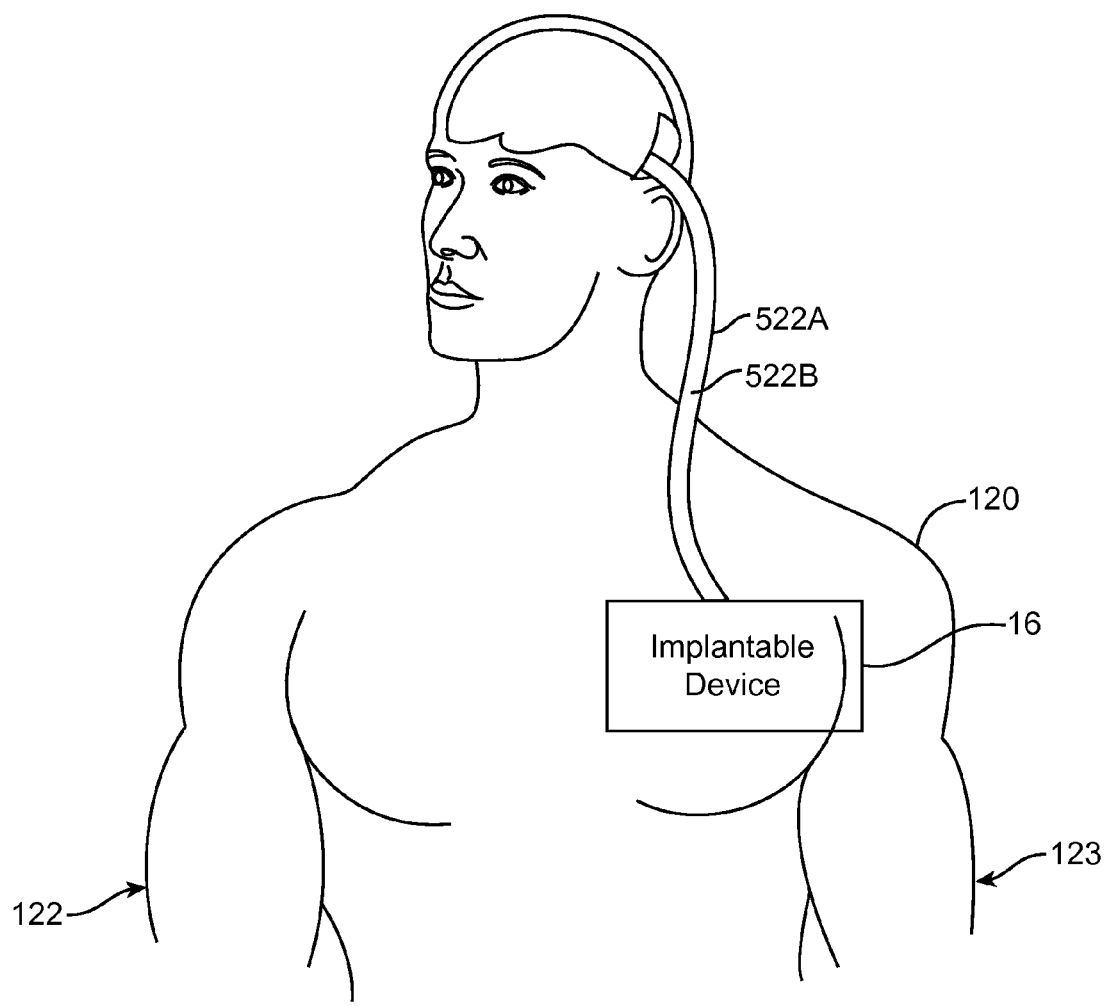

Referring to FIG. 2, in another embodiment, the system or device of the present invention may utilize drug delivery as the form of treatment therapy. A pump 10 may be implanted below the skin of a patient. The pump 10 has a port 14 into which a hypodermic needle can be inserted through the skin to inject a quantity of a liquid agent, such as a medication or drug. The liquid agent is delivered from pump 10 through a catheter port 20 into a catheter 422. Catheter 422 is positioned to deliver the agent to specific infusion sites in a brain (B). Pump 10 may take the form of any number of known implantable pumps including for example that which is disclosed in U.S. Pat. No. 4,692,147.

The distal end of catheter 422 terminates in a cylindrical hollow tube 422A having a distal end 425 implanted, by conventional stereotactic surgical techniques, into a portion of the brain to affect tissue within the Papez circuit or a downstream target of the Papez circuit (discussed above). Tube 422A is surgically implanted through a hole in the skull and catheter 422 is implanted between the skull and the scalp as shown in FIG. 2. Catheter 422 is joined to pump 10 in the manner shown. Pump 10 is implanted in a human body in a subcutaneous pocket located in the chest below the clavicle. Alternatively, pump 10 may be implanted in the abdomen.

Catheter 422 may be divided into twin tubes 422A and 422B (not shown) that are implanted into the brain bilaterally. Alternatively, tube 422B (not shown) implanted on the other side of the brain may be supplied with drugs from a separate catheter and pump.

Any number of drugs may be administered including, but not limited to, an anesthetic, a GABA agonist, a GABA antagonist, a glutamate antagonist, a glutamate agonist, a degrading enzyme, a reputake blocker, and a dopamine antagonist. An activating chemical may be used and includes any chemical that causes an increase in the discharge rate of the projection nerve cells from a region. An example (for projection neurons which receive glutamatergic excitation and GABA inhibition) would be an agonist of the transmitter substance glutamate (facilitating the excitation) or a GABA antagonist (blocking the inhibition). Conversely, a blocking chemical may be used and includes any chemical that inhibits the projection neurons thereby causing a decrease in the discharge rate of the projection nerve cells from a region. An example would be a glutamate antagonist (blocks excitatory input to the projection nerve cells) or a GABA agonist (enhances inhibition of the projection neurons).

A combination of treatment therapies may be delivered to provide influencing of various neuronal types. For example, it may be desirable to concurrently influence, via drug and/or electrical stimulation, the neurons in the hippocampus and other portions of the Papez circuit to achieve an improved result. Such a device to utilize both forms of treatment therapy may be that which is disclosed, for example, in U.S. Pat. No. 5,782,798. In addition to affecting the Papez circuit, it may be desirable to affect concurrently other portions of the brain.

Figure 3:
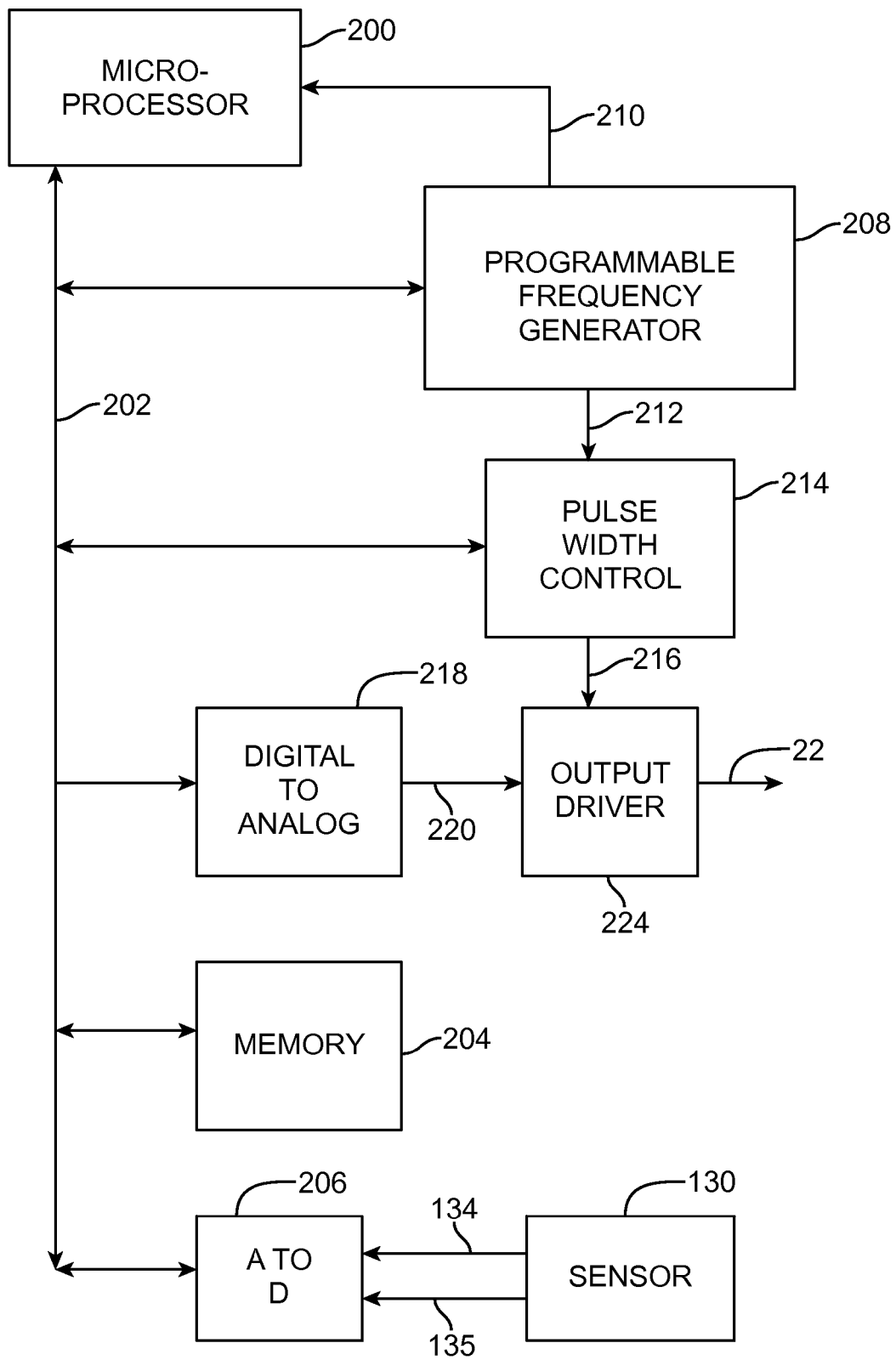
FIG. 3 is a schematic block diagram of a microprocessor and related circuitry of an implantable medical device for use with the present invention.

Referring to FIG. 3, the overall components of the implanted device 16 are shown (similar components may also be found for pump 10). The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 522 and lead 522A to the Papez circuit and/or other regions of the brain.

At the time the stimulation device 16 is implanted, the clinician programs certain key parameters into the memory of the implanted device via telemetry. These parameters may be updated subsequently as needed.

Hypothalamic stimulation has been found to modulate memory function and activate limbic structures. In particular, high frequency stimulation of the distal electrode contacts in the operating room and during the initial programming sessions evoked sensations of déjà vu and vague flashes of memory for the patient. After stimulation, the patient had shown significant improvements in memory tests that depended on hippocampal function. In particular, neuropsychological assessment conducted prior to the implantation of the DBS systems and 3 weeks after the electrodes were turned on revealed clear improvements on tests for learning and retention. In addition, post-operative associative recognition tasks revealed an increase in recollective retrieval with monopolar stimulation. Evoked responses were recorded with an electroencephalogram and reconstructed as low-resolution electromagnetic tomographic images. Source analysis showed that hypothalamic stimulation was spreading to the temporal lobes.

In particular, on the morning of the surgery, a stereotactic frame was applied to the patient's head under local anesthesia and a CT scan was obtained (MRI may also be used). The choice of the hypothalamic target (the ventromedial nucleus of the hypothalamus) to be stimulated was made based on indirect measurements from stereotactic atlas images relative to the anterior and posterior commissures. Deep brain stimulation electrodes (Medtronic model 3387; Medtronic, Minneapolis, Minn.) were bilaterally implanted and the four contacts of each of these electrodes were tested in the operating room. These contacts were numbered from 0-3 (right side) and 4-7 (left side), 0 and 4 being the most distal contacts and 3 and 7 the most proximal ones. The tips of the electrodes were positioned in a region where cells could still be recorded during microrecording mapping.

Sensations of déjà vu were reported with unilateral monopolar stimulation (cathode contact; anode case) of the two more distal contacts in each electrode (0, 1, 4 and 5), at 130 Hz, 60 microseconds of pulse width, and a threshold of 3-5 volts. Five months after the procedure, the patient returned for initial programming. With similar settings, the inventor was able to reproduce the stimulation related effects observed previously in the operating room. Déjà vu sensations occurred with high frequency stimulation when the most distal contacts (numbers 0 and 4) were activated. The threshold for this effect was 3.8V on each side of the brain.

The patient was programmed with the following parameters: Monopolar stimulation (cathode 0 and 4, anode case), 2.8V bilaterally, 130 Hz, and 60 microseconds. The neuropsychological evaluation was repeated 3 weeks after the electrodes were turned on. To assess the evoked responses and the areas that were activated with hypothalamic stimulation, a low-resolution electromagnetic tomography (LORETA) was obtained 1 month after the DBS electrodes were turned on.

Examining the pre-operative and 3 weeks post-stimulation results, baseline findings demonstrate that the patient had average to high average performances in most cognitive domains (abstraction, working memory, speed of processing, problem-solving, learning and retention). Even though little change was seen comparing post-stimulation with baseline scores, a clear improvement was observed on tests for learning and retention, such as the California Verbal Learning Test and the Petrides Spatial Learning Test.

At 4 months after operation, results were obtained of associative recognition tasks recorded without stimulation, with bipolar stimulation (2.8 V bilaterally, 60 μsec., 130 Hz, contacts 0 and 4 cathodes, and contacts 1 and 5 anodes) and with monopolar stimulation (2.8 V bilaterally, 60 μsec, 130 Hz, contacts 0 and 4 negative and case positive). There was a clear increase in the relative frequency of remember responses with monopolar stimulation, a condition/state that is modulated by hippocampus (recollective retrieval of associative information). Data from 10 healthy young volunteers have shown that the relative proportions of remember and know responses are respectively 0.45 and 0.55 (vs. 0.7 an 0.3 in the test patient).

The embodiments of the present invention shown above are open-loop systems. The microcomputer algorithm programmed by the clinician sets the stimulation parameters of signal generator 16. This algorithm may change the parameter values over time but does so independent of any changes in symptoms the patient may be experiencing. Alternatively, a closed-loop system discussed below which incorporate a sensor 130 to provide feedback could be used to provide enhanced results. Sensor 130 can be used with a closed loop feedback system in order to automatically determine the level of electrical stimulation necessary to achieve the desired level of improved cognitive function. In a closed-loop embodiment, microprocessor 200 executes an algorithm in order to provide stimulation with closed loop feedback control. Such an algorithm may analyze a sensed signal and deliver the electrical of chemical treatment therapy based on the sensed signal falling within or outside predetermined values or windows, for example, for BDNF and other neurotrophins (e.g., NGF, CNTF, FGF EGF, NT-3) and corticosteroids.

For example, in one embodiment, the patient may engage in a specified cognitive task and wherein the system measures one or more characteristics to determine if the sensed levels are at expected thresholds. If one or more of the sensed characteristics are outside a predetermined threshold, the system may initiate and/or regulate the treatment therapy to thereby enhance cognitive function.

In one embodiment, the system may be continuously providing closed-loop feedback control. In another embodiment, the system may operate in closed-loop feedback control based on a time of day (e.g., during hours that the patient is awake) or based on a cognitive task (e.g., when the patient is working). In yet another embodiment, the system may be switchable between open-loop and closed-loop by operator control.

In another embodiment, the stimulation or drug delivery could be applied before, after and/or during the performance of a memory, cognitive or motor task learning task to facilitate the acquisition of learning or consolidation of the task and in so doing, accelerate the rate of memory acquisition and learning and enhance its magnitude. For example, the stimulation or drug delivery may be provided before, during, or after periods when the patient is learning a new language or playing a new instrument. Such therapy may be useful during the encoding, consolidation and/or retrieval phases of memory. The neuromodulation intervention, brain stimulation or drug delivery could occur before, after or simultaneously to the memory, cognitive of motor skill task.

In another embodiment, therapy may be provided in relation to a learning task. For example, the stimulation or drug delivery could be applied before, after and/or during the performance of a memory, cognitive or motor task to facilitate the acquisition of learning or consolidation of the task. In so doing, the rate of memory acquisition and learning may be accelerated and enhanced in magnitude. For example, the stimulation or drug delivery may be provided before, during, or after periods when the patient is learning a new language or playing a new instrument. Such therapy may be useful during the encoding, consolidation and/or retrieval phases of memory. The neuromodulation intervention, brain stimulation or drug delivery could occur before, after or simultaneously to the memory, cognitive of motor skill task.

In another aspect of the invention, treatment therapy may be utilized to enhance neurogenesis as a method of improving cognitive function. Techniques for enhancing neurogenesis through treatment therapy are disclosed in a co-pending patent application entitled "Enhancing Neurogenesis Within A Human Brain," filed concurrent with the instant application and incorporated herein by reference in its entirety.

Referring back to FIG. 3, the system may optionally utilize closed-loop feedback control having an analog to digital converter 206 coupled to sensor 130. Output of the A-to-D converter 206 is connected to microprocessor 200 through peripheral bus 202 including address, data and control lines. Microprocessor 200 processes sensor data in different ways depending on the type of transducer in use and regulates delivery, via a control algorithm, of electrical stimulation and/or drug delivery based on the sensed signal. For example, when the signal on sensor 130 exceeds a level programmed by the clinician and stored in a memory 204, increasing amounts of stimulation may be applied through an output driver 224. In the case of electrical stimulation, a parameter of the stimulation may be adjusted such as amplitude, pulse width and/or frequency.

Parameters which could be sensed include the activity of single neurons as detected with microelectrode recording techniques, local field potentials, event related potentials, for example in response to a memory task or sensory stimulus and electroencephalogram or electrocorticogram. For example, U.S. Pat. No. 6,227,203 provides examples of various types of sensors that may be used to detect a symptom or a condition of a cognitive disorder and responsively generate a neurological signal. In an embodiment, a neurochemical characteristic of the cognitive function may be sensed, additionally or alternatively. For example, sensing of local levels of neurotransmitters (glutamate, GABA, Aspartate), local pH or ion concentration, lactate levels, local cerebral blood flow, glucose utilization or oxygen extraction may also be used as the input component of a closed loop system. These measure could be taken at rest or in response to a specific memory or cognitive task or in response to a specific sensory or motor stimulus. In another embodiment, an electro-physiological characteristic of the cognitive function may be sensed. The information contained within the neuronal firing spike train, including spike amplitude, frequency of action potentials, signal to noise ratio, the spatial and temporal features and the pattern of neuronal firing, oscillation behavior and inter-neuronal correlated activity could be used to deliver therapies on a contingency basis in a closed loop system. Moreover, treatment therapy delivered may be immediate or delayed, diurnal, constant or intermittent depending on contingencies as defined by the closed loop system.

Thus, embodiments of IMPROVING COGNITIVE FUNCTION WITHIN A HUMAN BRAIN are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for treating human cognitive disorders by means of an implantable signal generator and a lead having a proximal end coupled to the signal generator and a distal portion having at least one electrode, the method comprising:
   (a) implanting at least one electrode in a brain so that the stimulation portion is within tissue elements of the Papez circuit selected from the group consisting of the fornix and the mammilothalamic tracts;
   (b) coupling the proximal end of the implanted electrode to the signal generator; and
   (c) treating the cognitive disorder by operating the signal generator to deliver stimulation to the tissue elements.

2. A method as claimed in claim 1, wherein (c) is performed in relation to a learning task.

3. A method as claimed in claim 2, wherein the learning task is selected from the group consisting of a memory task, a cognitive task, and a motor task.

4. A method, as claimed in claim 1, wherein (a) comprises bilaterally implanting at least two electrodes.

5. A method, as claimed in claim 1, wherein (c) comprises selecting amplitude, width and frequency of stimulation by the electrode.

6. A method, as claimed in claim 1, wherein (c) comprises operating the signal generator to pulse at a frequency of up to 300 Hertz.

7. A method, as claimed in claim 1, wherein (c) comprises operating the signal generator to pulse at a pulse amplitude of up to 10 Volts.

8. A method, as claimed in claim 1, wherein (c) comprises operating the signal generator to pulse at a pulse width of up to 400 μseconds.

9. A method as claimed in claim 1, further comprising:
   (d) sensing a characteristic indicative of the extent of the cognitive disorder and generating a sensor signal; and
   (e) regulating the operation of the signal generator in response to the sensor signal.

10. A method, as claimed in claim 9, wherein (d) comprises detecting a neurochemical characteristic of the cognitive disorder.

11. A method, as claimed in claim 9, wherein (d) comprises detecting a neurochemical characteristic selected from the group consisting of a neurotransmitter level, a pH concentration, an ion concentration, a lactate level, cerebral blood flow, glucose utilization, and oxygen extraction.

12. A method, as claimed in claim 9, wherein (d) comprises detecting an electrophysiological characteristic of the cognitive disorder.

13. A method, as claimed in claim 12, wherein (d) comprises detecting an electrophysiological characteristic selected from the group consisting of the activity of single neurons, local field potentials, event related potentials, an electroencephalogram, and an electrocorticogram.

14. A method as claimed in claim 9, wherein (e) comprises executing a control algorithm.

15. A method, as claimed in claim 10, wherein (e) comprises adjusting at least one parameter of the stimulation, the parameter being selected from the group consisting of amplitude, pulse width and frequency.

16. A method as claimed in claim 1, further comprising:
   (d) sensing a characteristic indicative of the extent of the cognitive disorder and generating a sensor signal; and
   (e) if the sensor signal is outside of a predetermined threshold, treating the cognitive disorder by initiating stimulation therapy by the signal generator.

17. A method, as claimed in claim 1, further comprising:
   (d) implanting at least one secondary electrode so that a secondary stimulation portion lies in communication with a predetermined portion of a brain;
   (e) coupling the secondary electrode to the signal generator; and
   (f) operating the signal generator to stimulate the brain.

18. A method, as claimed in claim 1, further comprising:
   (d) implanting at least one catheter so that a secondary stimulation portion lies in communication with the tissue elements wherein the tissue elements are selected from the group consisting of tissue within a Papez circuit of a human brain, tissue within a downstream target of the Papez circuit, and tissue within an upstream input to the Papez circuit;
   (e) coupling the catheter to a pump; and (f) operating the pump to deliver drug to the brain to thereby treat the cognitive disorder in the human.

19. The method of claim 1, wherein the cognitive disorder is selected from the group consisting of Alzheimer's disease, mild cognitive impairment (MCI), dementia, amnesia, and memory disorder.

20. The method of claim 19, wherein said cognitive disorder is Alzheimer's disease.

21. The method of claim 19, wherein said cognitive disorder is MCI.

22. The method of claim 1, wherein said cognitive disorder is selected from the group consisting of amnestic syndromes, Werkicke-Korsakoff syndrome, Korsakoff syndrome, Herpes encephalitis, severe hypoxia, vascular disorders, head injury, transient global amnesia, global amnesia epileptic amnesia, cerebral palsy, autism, mental retardation, attention deficit disorder and hyperactivity disorders.

23. The method of claim 1, wherein the tissue element is the fornix.

24. The method of claim 1, wherein the tissue element is the mammilothalamic tracts.

25. A method for the improvement of cognitive function in a human having Alzheimers disease and/or mild cognitive impairment (MCI) by means of an implantable signal generator and a lead having a proximal end coupled to the signal generator and a distal portion having at least one electrode, the method comprising:
(a) implanting at least one electrode in a brain so that the stimulation portion is within tissue elements of the Papez circuit selected from the group consisting of the fornix and the mammilothalamic tracts;
(b) coupling the proximal end of the implanted electrode to the signal generator; and improving cognitive function by the human by operating the signal generator to deliver stimulation to the tissue elements.

26. The method of claim 25, wherein the tissue element is the fornix.

27. The method of claim 25, wherein the tissue element is the mammilothalamic tracts.

* * * * *